United States Patent
Branch et al.

(10) Patent No.: US 9,980,693 B2
(45) Date of Patent: May 29, 2018

(54) IMAGING PROXY

(71) Applicant: ERMI, Inc., Atlanta, GA (US)

(72) Inventors: Thomas P. Branch, Atlanta, GA (US); Shaun K. Stinton, Chamblee, GA (US); Edward Dittmar, Marietta, GA (US); Nathaniel K. DeJarnette, Lilburn, GA (US)

(73) Assignee: ERMI, Inc., Atlanta, GA (US)

( * ) Notice: Subject to any disclaimer, the term of this patent is extended or adjusted under 35 U.S.C. 154(b) by 451 days.

(21) Appl. No.: 14/603,924

(22) Filed: Jan. 23, 2015

(65) Prior Publication Data

US 2015/0202022 A1 Jul. 23, 2015

Related U.S. Application Data

(60) Provisional application No. 61/930,910, filed on Jan. 23, 2014.

(51) Int. Cl.
| | |
|---|---|
| *A61B 5/00* | (2006.01) |
| *A61B 6/00* | (2006.01) |
| *A61B 5/055* | (2006.01) |
| *A61B 6/03* | (2006.01) |
| *A61B 8/08* | (2006.01) |
| *A61B 5/11* | (2006.01) |
| *A61B 90/00* | (2016.01) |
| *G01R 33/28* | (2006.01) |

(52) U.S. Cl.
CPC ............ *A61B 6/487* (2013.01); *A61B 5/055* (2013.01); *A61B 5/1114* (2013.01); *A61B 5/1127* (2013.01); *A61B 6/032* (2013.01); *A61B 8/085* (2013.01); *A61B 90/39* (2016.02); *A61B 2090/3925* (2016.02); *A61B 2090/3937* (2016.02); *A61B 2090/3954* (2016.02); *A61B 2090/3966* (2016.02); *G01R 33/28* (2013.01)

(58) Field of Classification Search
CPC ..... A61B 17/1764; A61B 90/36; A61B 34/10; A61B 2034/107; A61B 2034/105
See application file for complete search history.

(56) References Cited

U.S. PATENT DOCUMENTS

| | | | |
|---|---|---|---|
| 7,291,119 B1 | 11/2007 | de Guise et al. | |
| 7,782,997 B2 | 8/2010 | Koehler et al. | |
| 2005/0085714 A1* | 4/2005 | Foley | A61B 34/20 600/424 |

(Continued)

FOREIGN PATENT DOCUMENTS

WO 2007004195 A2 1/2007

OTHER PUBLICATIONS

PCT International Preliminary Search Report on Patentability dated Jul. 26, 2016 for corresponding PCT/US2015/012571.

(Continued)

*Primary Examiner* — Joel Lamprecht
(74) *Attorney, Agent, or Firm* — Lempia Summerfield Katz LLC

(57) ABSTRACT

A method includes disposing an object relative to a first body, positioning a second body within a field of view of an imaging system such that the object is within the field of view and the first body is outside the field of view, and capturing, by the imaging system, data indicative of the object and the second body.

25 Claims, 13 Drawing Sheets

(56) References Cited

U.S. PATENT DOCUMENTS

| | | |
|---|---|---|
| 2005/0085715 A1* | 4/2005 | Dukesherer .............. A61B 5/06 |
| | | 600/424 |
| 2006/0025677 A1* | 2/2006 | Verard ................... A61B 5/062 |
| | | 600/423 |
| 2006/0084867 A1* | 4/2006 | Tremblay ............... A61B 90/36 |
| | | 600/434 |
| 2006/0142657 A1 | 6/2006 | Quaid et al. |
| 2011/0174314 A1* | 7/2011 | Miyazaki ............... A61B 90/50 |
| | | 128/845 |
| 2012/0046540 A1 | 2/2012 | Branch et al. |
| 2013/0201563 A1 | 8/2013 | Nunnink et al. |
| 2013/0294570 A1 | 11/2013 | Hansis |

OTHER PUBLICATIONS

"Orientierungstauchen Wikipedia", retrieved from https://de.wikipedia.org on Mar. 24, 2015 with English translation.
International Search Report and Written Opinion from PCT/US2015/012571, Apr. 1, 2015, WO.

\* cited by examiner

IMAGING PROXY

This application claims priority under 37 C.F.R. § 1.19(e) to U.S. Provisional Patent Application No. 61/930,910, entitled "Imaging Proxy Device and Methods for Using Same," and filed Jan. 23, 2014, the entire disclosure of which is hereby incorporated by reference.

FIELD

The disclosure relates generally to imaging techniques.

BACKGROUND

The field of view ("FOV") of an imaging system establishes the extent to which image data is captured at a given time or acquisition event. Imaging systems often have a narrow FOV, such as 1-2 centimeters. A narrow FOV may be addressed by capturing scan data for multiple slices over a longer period of time. For example, the position of the table supporting the subject may be adjusted. Larger, e.g., three-dimensional, images are then constructed from the smaller slices.

Various attempts have been made to extend the FOV of imaging systems. Some techniques are directed to removing distortion. Other techniques involve mirrors that reflect light onto the image plane. Also, extending a FOV may result in exposing objects within the extended FOV to larger amounts of radiation in some modalities of imaging.

SUMMARY OF THE DISCLOSURE

The scope of the present invention is defined solely by the appended claims and is not affected to any degree by the statements within this summary.

In one aspect, a method includes disposing an object relative to a first body such that the object acts as an imaging proxy for the first body, positioning a second body within a field of view of an imaging system such that the object is within the field of view and the first body is outside the field of view, and capturing, by the imaging system, data indicative of the object and the second body.

In another aspect, an imaging system includes a scanner configured to capture scan data within a field of view and an imaging proxy including a coupler configured for rigid attachment of the imaging proxy to a first body outside of the field of view, and further including an object connected to the coupler and spaced from the first body for detection by the scanner such that the scan data is indicative of a position of the object within the field of view. The imaging system further includes a processor configured to determine, based on the scan data, a position of the first body relative to a second body disposed in the field of view.

In yet another aspect, an imaging proxy includes a coupler configured for rigid attachment of the imaging proxy to a body, a riser attached to the coupler, and an object attached to the riser. The object includes first and second extensions oriented at respective angles relative to the coupler. The first and second extensions extend away from the coupler, and a height of the riser is adjustable to establish an offset of the coupler and the object.

BRIEF DESCRIPTION OF THE DRAWING FIGURES

For a more complete understanding of the disclosure, reference should be made to the following detailed description and accompanying drawing figures, in which like reference numerals identify like elements in the figures.

Figure 1:
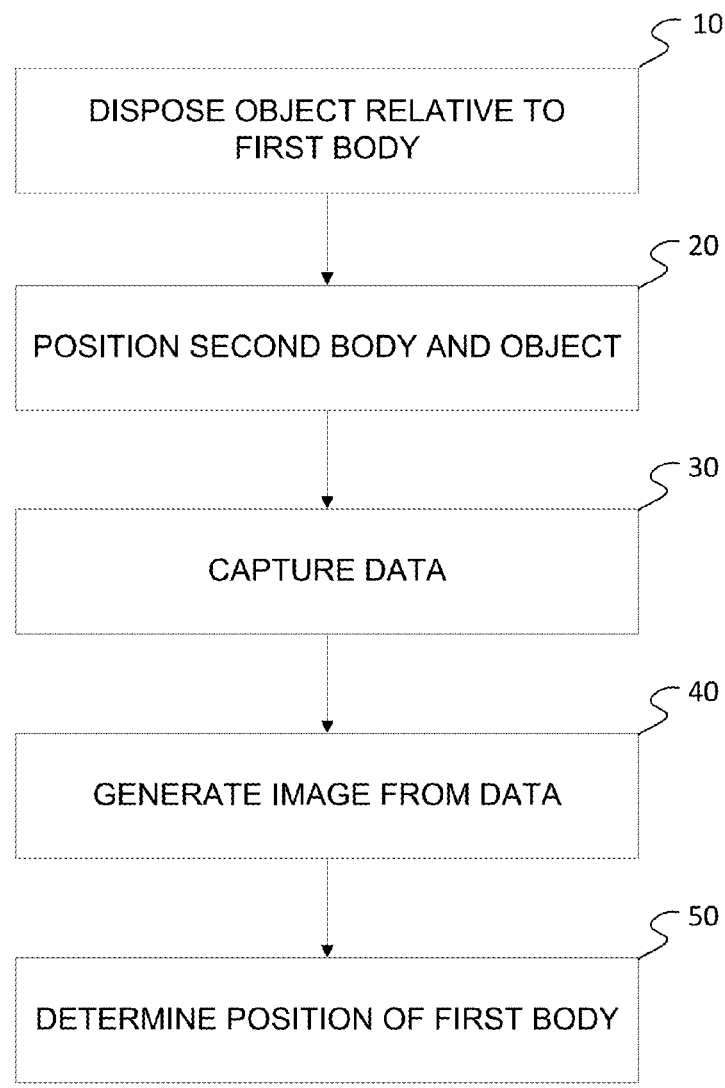
FIG. 1 is a flow chart diagram of a method of imaging using a proxy in accordance with one embodiment.

While the disclosed systems and methods are susceptible of embodiments in various forms, there are illustrated in the drawing (and will hereafter be described) specific aspects of the invention, with the understanding that the disclosure is intended to be illustrative, and is not intended to limit the invention to the specific embodiments described and illustrated herein.

DETAILED DESCRIPTION

Imaging methods, systems, and apparatus are described to provide an imaging proxy for a body outside of the field of view ("FOV") of the imaging system. The imaging proxy may project an identifiable structure into the FOV of the imaging system, thereby establishing a surrogate of the body. The imaging proxy may thus allow the position of the body to be known despite being outside of the FOV. The location and/or orientation of the body may then be determined relative to one or more structures within the FOV. Imaging of the proxy provides an indication of the position of the body because of a determined and/or established geometric relationship between the proxy and the body. Various benefits may result from the implementation of imaging proxies. For example, proxies may be sized so as to allow for smaller scanning areas that would be required to scan larger bodies, or groups of bodies. As such, and given the radiation used to scan areas and volumes of bodies, the radiation exposure may be focused on the proxy, and not a body of interest.

The imaging proxy may useful in connection with imaging a singular body. The imaging proxy may also be useful in connection with two or more bodies, such as anatomical body parts, in motion relative to one another. The relative location and/or orientation of the body parts may be analyzed over time. The imaging methods may thus include motion of the body parts during scanning or other data capture by the imaging system. Such motion may be useful in analyzing the biomechanics of an anatomical structure, such as the knee or other joint.

The imaging proxy is disposed relative to a body, such as a mechanical or anatomical structure, outside of the FOV of the imaging system. For instance, the imaging proxy may be fixedly or rigidly secured or attached to the body. Alternatively or additionally, the imaging proxy may be registered with the body. In some cases, the imaging proxy includes a coupling, such as a strap, to attach the imaging proxy to a leg or other body part outside of the FOV. Other couplings may involve or include adhesive attachment.

The imaging proxy may establish the position and/or orientation of the body outside of the FOV relative to one or more bodies inside the FOV. The position may be provided via the projection of the imaging proxy into the FOV. In this way, the relative position of an anatomical structure outside of the FOV may be established through association with the imaging proxy. Multiple imaging proxies or proxy segments may be used to establish the relative positions of multiple bodies outside of the FOV.

Although described in connection with examples involving legs and bones connected at the knee of a subject, the disclosed methods, systems, and devices are not limited to imaging involving a leg or knee. The imaging proxy techniques of the disclosed embodiments are well suited for use in connection with a variety of different bodies or body parts. For instance, the imaging proxy techniques may be used to determine the relative positions of body parts at other joints, such as those at elbows, fingers, shoulders, hips, spine, and feet.

In an embodiment, image and/or scan data including merely the proxy (i.e. no second object) may be used to determine a location of a singular body when not in a FOV of an imaging system. In this embodiment, multiple images may be generated at different times for the FOV with the body in a different position at each time. The position of the object at each of the times may be determined from the representation of the proxy the FOV at the times.

FIG. 1 depicts a flow chart diagram of a method of imaging with a proxy. The method includes disposing an object relative to a first body (block 10), positioning a second body and the object (block 20), capturing data (block 30), generating or displaying an image (block 40), and determining a position of the first body (block 50). Additional, different, or fewer acts may be provided. For example, an image may not be generated in some cases. The acts are performed in the order shown or other orders. For example, the position of the first body may be determined before or during the generation of the image. As another example, the second body and the object may be positioned before or while the object is disposed relative to the first body. One or more of the acts may be repeated.

The disposition of the object relative to the first body (block 10) may include rigidly or otherwise fixably securing an imaging proxy to the first body. The imaging proxy includes the object. In some cases, the object may be fixably connected or attached via a coupler of the imaging proxy, such as an attachment section 120 described in connection with the embodiments depicted in FIGS. 5-7. The coupler may be fixably secured to the first body through other techniques. For example, the coupler may establish the attachment using bolts, screws, adhesives, and/or any other attachment technique operable to maintain the connection and relative placement of the object and the first body.

A body, i.e. the first, second and/or third or other bodies, may involve any type of body, such as mechanical, anatomical, structural, or geographical bodies or combinations thereof. The bodies may be connected or otherwise constrained in relative movement. The bodies may also unconnected and free to move in any of six ("6") degrees of freedom relative to each other. The 6 degrees of freedom involve translations and rotations about three perpendicular axis established in space.

The object may include, or be composed of, a material that is detectable by the imaging system. For example, the object may include borosilicate glass, wood, plastic, metal, ceramic, and/or other materials or combinations thereof depending on the imaging and/or scanning modality used.

In some cases, the object is elongate. For example, the object may be rod-shaped or otherwise include a rod. The rod may extend from the first body to reach the FOV. The object may have any size, shape, construction, or configuration capable of serving as a proxy or surrogate for the first body. As a proxy, the object may provide spatial information and/or orientation information. The structure of the object may vary. In some cases, the object may include a projecting structure or other projection. For example, the projecting structure may be a rod or multiple rods. Also, the object may include one or more reference structures. Each reference structure may have a distinct shape. The shape may be used as a reference point, which may allow the position of the first body to be identified. For example, the reference structure may be rectangular or triangular. Reference may be made to the edges and/or corners of such shapes so as to indicate a rotational position of the first body. Also, a circular disk or square shape may be used so as to provide a point reference to the position of the first body.

A point reference may be used to determine a linear position of the first object. Appropriately oriented square and or triangular shapes may also be used to indicate a linear position of the first object. Any shape that may convey information about orientation may be used in conjunction with or as an alternative to a protruding rod. Also, the object may involve multiple extensions, protruding rods, and/or other structures oriented relative to the first body. The orientation of the multiple extensions, protruding rods, and/or other structures may indicate a linear and/or rotational position of the first body.

The second body and the object are positioned (block 20) within the FOV of the imaging system. The first and second bodies are configured such that the first body is outside the FOV while the second body and the object are inside the FOV. In some cases, positioning the second body within the field of view involves positioning the object such that at least a first extension and a second extension of the object intersect the FOV at a first location and a second location, respectively.

The FOV may be defined or established via the configuration of the imaging system. A field of view may correspond with a useful area or volume capable of being scanned or viewed. The area or volume may be established by field limiting devices of the imaging system, such as X-ray collimators, or by an extent of an area or volume that may be represented by scan data in an undistorted, or sufficiently undistorted, manner.

In some cases, positioning the second body and the object may include a registration process that registers the positional relationships between the first body and the object. The registration process may also register the positional relationship of the second body. Further information regarding exemplary registration processes are described in connection with FIG. 9.

Slice, scan or other data may be captured (block 30) by the imaging system. The data may be captured using any imaging technique or modality. For example, the imaging system may be or include an ultrasound scanner, computed tomography (CT), fluoroscopy, or other X-ray scanner, a magnetic resonance imaging (MRI) system, optical scanner, infrared scanner, magnetic tracking, and/or other imaging systems. In some cases, the imaging system may be a hybrid or multiple modality imaging system, in which two or more imaging techniques are used to capture the data. The scanner may use any type of electromagnetic emission (including one or more parts of the electromagnetic spectrum, such as optical wavelengths and x-rays), nuclear emission, or other emission to capture the scan data.

The captured data is representative or indicative of structures, such as the object and the second body, disposed within the FOV of the imaging system. The structures may include any type of tissue or body part, including, for instance, the material of bones, ligaments, tendons, and muscles. The captured data may be two-dimensional or three-dimensional data. In some cases, the captured data is representative of multiple slices scanned by the imaging system.

The captured data may be indicative of motion of the first body and/or the second body. The first and/or second bodies may thus be moving during the data capture. In some cases, the movement may occur while the imaging system is scanning to capture the data. In such cases, the imaging system has a frame rate capable of resolving the motion. Alternatively or additionally, the movement occurs between respective scans used to capture the data. In such cases, the frame rate of the imaging system may not be capable of resolving the motion.

An image may be displayed or otherwise generated (block 40). The image may be generated from the captured data. The image may be generated using any technique operable to render, display or otherwise generate a visible representation of structures represented by the captured data. A variety of image rendering techniques may be used, including, for instance, various types of two-dimensional and three-dimensional reconstructions, projections, and overlays. The image may include multiple representations of the object and the second body.

A position of the first body may be determined (block 50). The position of the first body may be determined from data indicative of the object, such as the captured data (Block 30). In some cases, the position of the first body may be determined after the captured data is used to generate an image. The position of the first body may be determined from the representation of the object in the image. In another embodiment, the captured data may be used to determine the position of the first body without the use of an image. In an embodiment, the absolute location of the first object may be determined in each or any of 6 degrees of freedom. In another embodiment, a location of the first body relative to the second body may be determined in each or any of 6 degrees of freedom.

In some cases, the image may be modified to include a representation of the first body. Despite being outside of the FOV, a representation of the first body may be overlaid or otherwise superimposed upon the image generated from the scan data. For example, the image may be extended to depict the representation of the first body. The representation of the first body may be derived from the position data determined in block 50.

The data capture may be repeated. Any number of scans of the FOV may be implemented. The multiple scans may involve different positions of the first body relative to the second body. For example, the first body may undergo a rotation and/or a translation relative to the second body. In some cases, the position of the second body does not change. The data representing the object from each scan may be used to determine the position of the first body in each respective scan. Images may then be generated or displayed of the multiple scans.

Figure 2A:
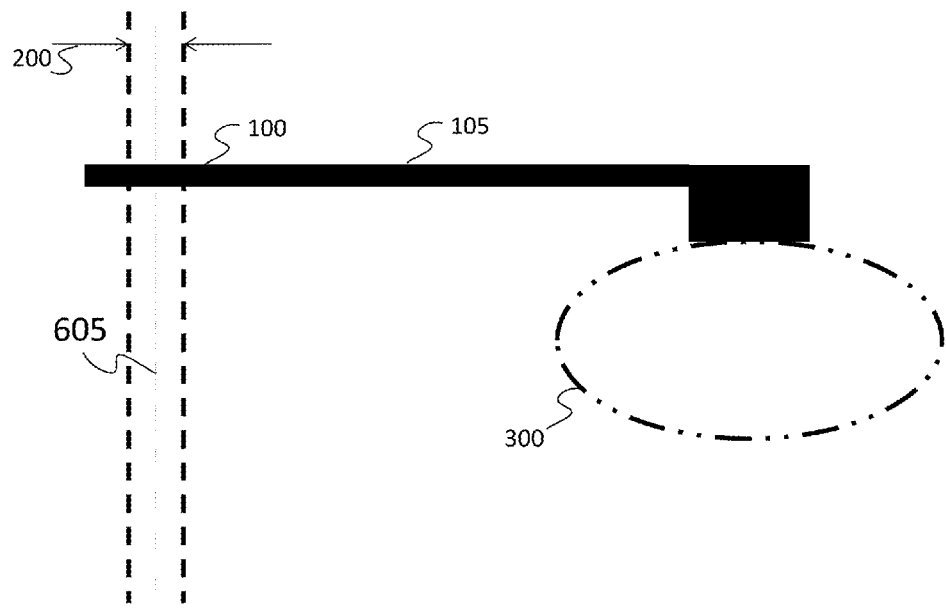
FIGS. 2A and 2B are schematic diagrams of an imaging proxy in accordance with one embodiment.

FIG. 2A shows an exemplary embodiment of an imaging proxy 100. In this case, an imaging system has an imaging FOV schematically depicted at 200. A body of interest 300 is disposed outside of the imaging FOV 200. The imaging proxy 100 is coupled or attached to the body 300. Exemplary couplings and attachments are described below. The imaging proxy 100 extends from the object to reach the imaging FOV 200. The imaging proxy 100 is thus disposed within the imaging FOV 200 as shown. The imaging proxy 100 includes an object 105 that intersects a plane 605 within the imaging FOV 200. In some cases, the plane 605 corresponds with a two-dimensional slice of the imaging FOV 200. The plane 605 does not intersect the body 300. In this embodiment, the location of the body of interest 300 is known through the representation of the imaging proxy 100 in the FOV 200.

Figure 2B:
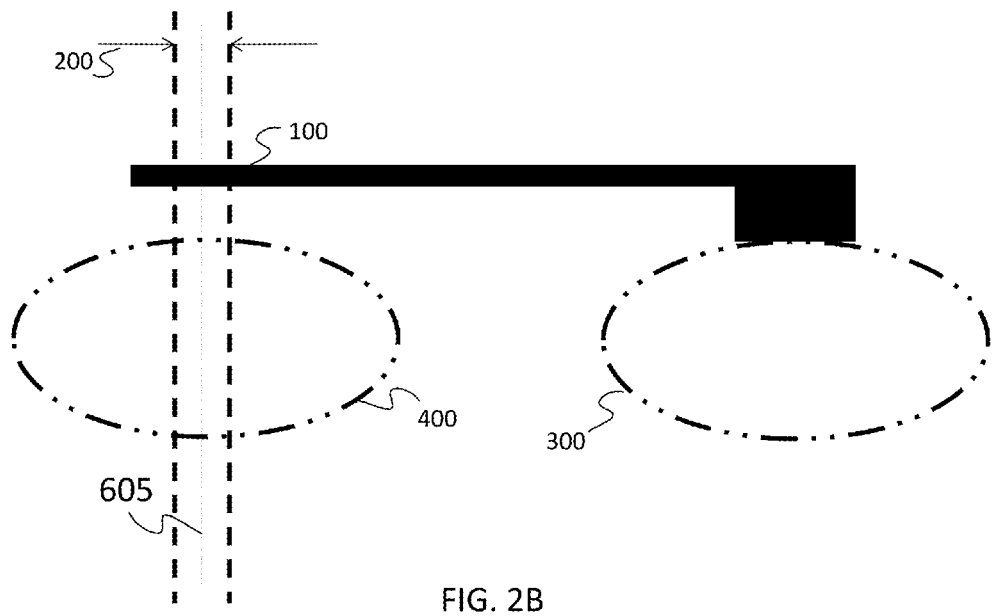

FIG. 2B shows the embodiment of FIG. 2A with a second body 400. The second body 400 is disposed within the imaging FOV 200. The imaging proxy 100 is still disposed within the imaging FOV 200, and the body 300 remains outside the imaging FOV 200. The plane 605 is defined such that the plane 605 intersects both the imaging proxy 100 and the second body 400. Positioning the imaging proxy 100 and the second body 400 such that the plane 605 is within the FOV 200 allows the imaging system to capture data representative of both the imaging proxy 100 and the second body 400 in a scan of the FOV, while the body 300 is not included in the scan.

Figure 3:
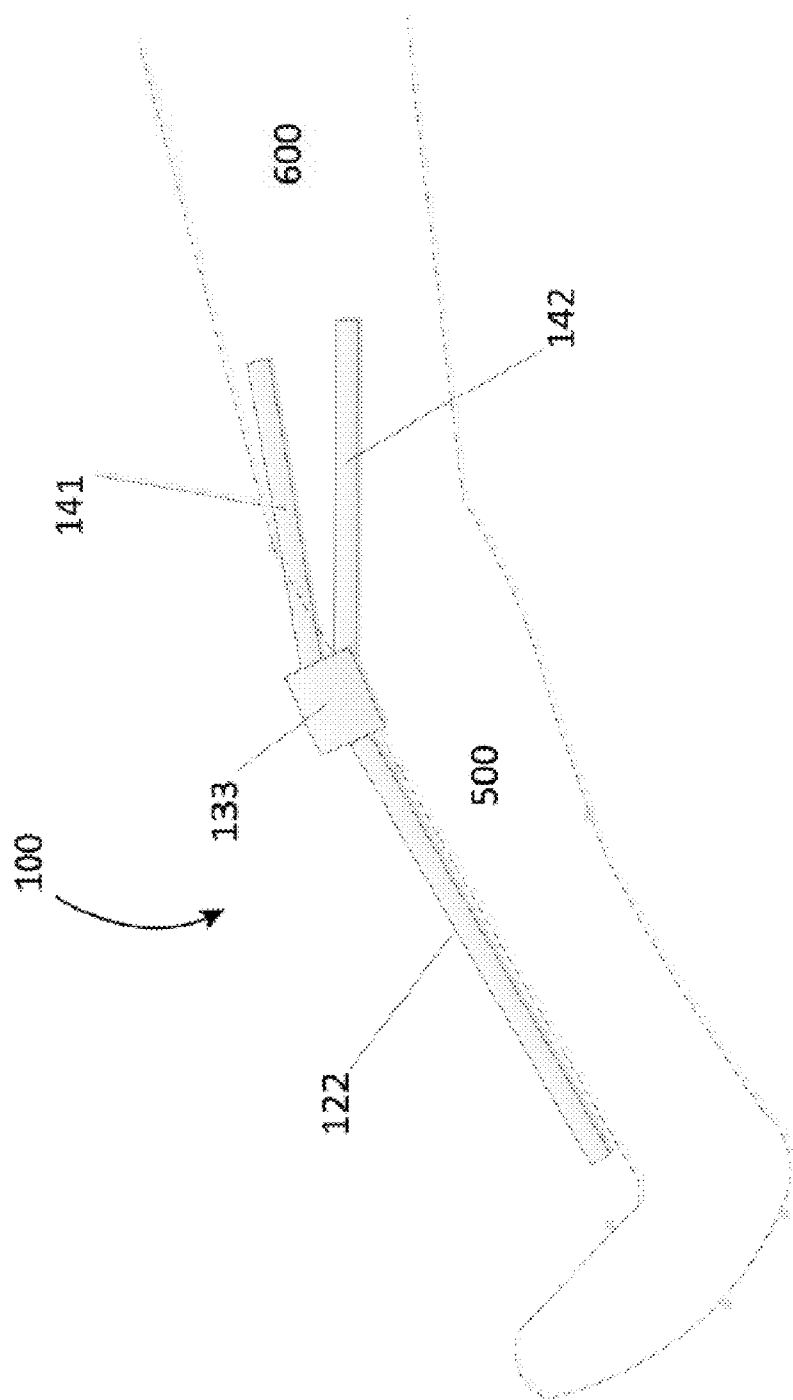
FIG. 3 is a schematic, side view of an exemplary imaging proxy disposed relative to a leg in accordance with one embodiment.

FIG. 3 is a schematic, side view of an exemplary embodiment in which the imaging proxy 100 is positioned relative to a lower leg 500 and an upper leg 600 of a subject. In this case, the imaging proxy 100 includes a frame bar 122, a mounting block 133, and detectable bars 141, 142 extending outward from the mounting block 133. The detectable bars 141, 142 extend from the lower leg 500 to indicate the position of the lower leg 500 relative to the upper leg 600. In this case, the detectable bars 141, 142 are sized such that each bar 141, 142 extends beyond the knee of the subject to overlap the upper leg 600. In other cases, one or both of the detectable bars 141, 142 may overlap the knee rather than the upper leg 600.

The shape and other characteristics of the bars 122, 141, 142 may vary. For example, one or more of the bars 122, 141, 142 may have a rounded cross-section and, thus, be rod-shaped. The cross-section of the detectable bars 141, 142 may vary along the length thereof to provide one or more reference features.

Each detectable bar 141, 142 may be oriented at an angle relative to the frame bar 122. The angle may be predetermined or otherwise known. The detectable bars 141, 142 may be disposed in a V-shape as shown. The angled offset of the detectable bars 141, 142 may vary and/or be adjustable. For example, in some cases and/or some deployments, one of the detectable bars 141, 142 may be aligned with the frame bar 122, while the other one of the detectable bars 141, 142 may be non-aligned with the frame bar 122.

In the example of FIG. 3, the frame bar 122 may be fixedly or rigidly secured to the lower leg 500 via any type of attachment. For instance, the frame bar 122 may be adhesively secured to the lower leg 500. Alternatively or additionally, the imaging proxy 100 may include one or more couplers, connectors, and/or other components configured to secure the frame bar 122 to the lower leg 500, examples of which are described below in connection with FIG. 4.

Figure 4:
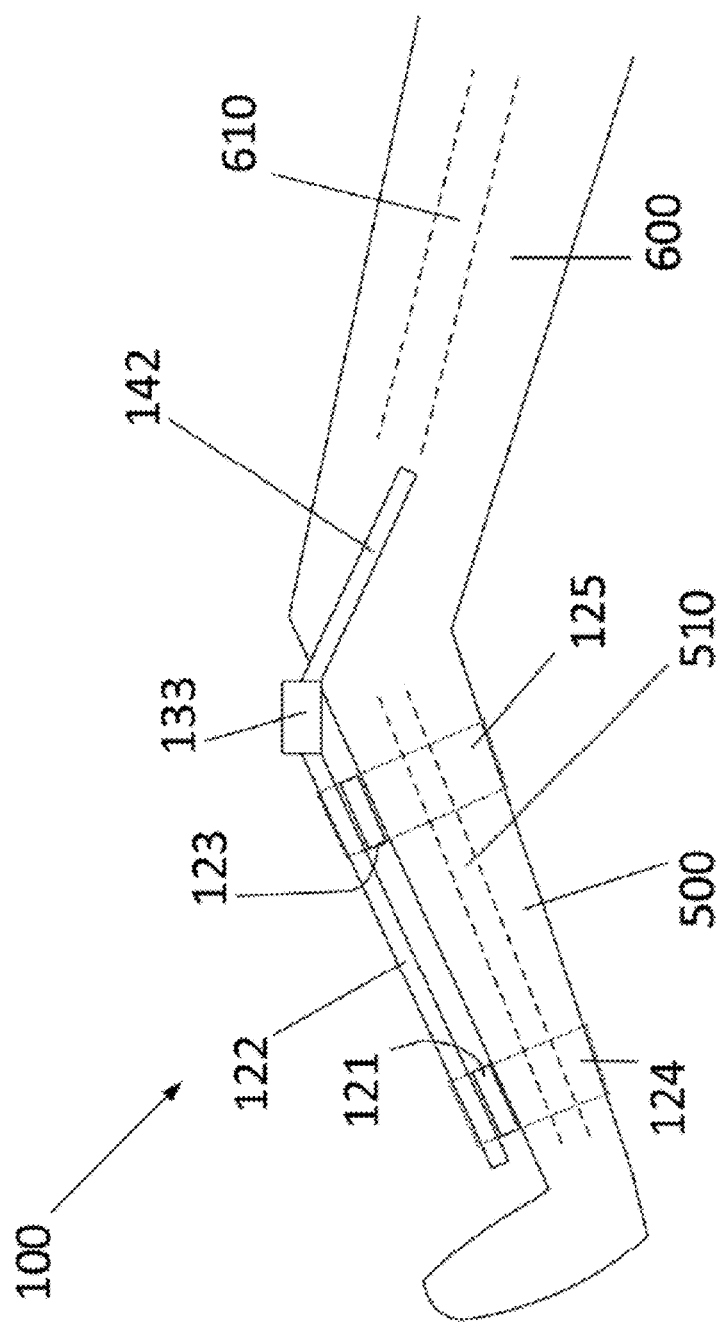
FIG. 4 is a schematic, side view of another exemplary imaging proxy disposed relative to a leg in accordance with one embodiment.

FIG. 4 is a schematic, side view of an exemplary embodiment in which the imaging proxy 100 is attached to the lower leg 500 with a distal attachment 121 and a proximal attachment 123. The distal and proximal attachments 121, 123 engage the frame bar 122 and the lower leg 500 at distal and proximal positions relative to the FOV, respectively. In this case, the detectable bar 142 is positioned to extend along a lateral side of the knee toward the upper leg 600. The other detectable bar 141 (FIG. 3) may be positioned and extend along the other lateral side of the knee toward the upper leg 600.

In the example of FIG. 4, each attachment 121, 123 includes a respective strap 124, 125 configured to secure the frame bar 122 to the lower leg 500. Each strap 124, 125 may include a respective loop in which the frame bar 122 is captured. The loops may be disposed in a central section of the strap 124, 125. Each strap 124, 125 may include sections with complementary hook-and-loop or other fasteners at or near ends of the straps 124, 125 to be engaged once the straps 124, 125 are wrapped around the lower leg 500. The straps 124, 125 may alternatively or additionally include fasteners in the form of buckles (e.g., belt buckles), snap-fit connectors, rings, and/or other bindings.

As shown in FIG. 4, the frame bar 122 is aligned with a tibia 510 of the lower leg 500. The detectable bar 142 (and/or the detectable bar 141 as shown in FIG. 3) protrudes away from the frame bar 122, the tibia 510, and the mounting block 133 into a space shared by the upper leg 600 and femur 610. During scanning, the FOV of the imaging system may pass through the femur 610 and the detectable bar 142, but not the tibia 510. The detectable bar 142 allows the position and/or orientation of the tibia 510 to be determined despite being outside of the FOV.

Figure 5:
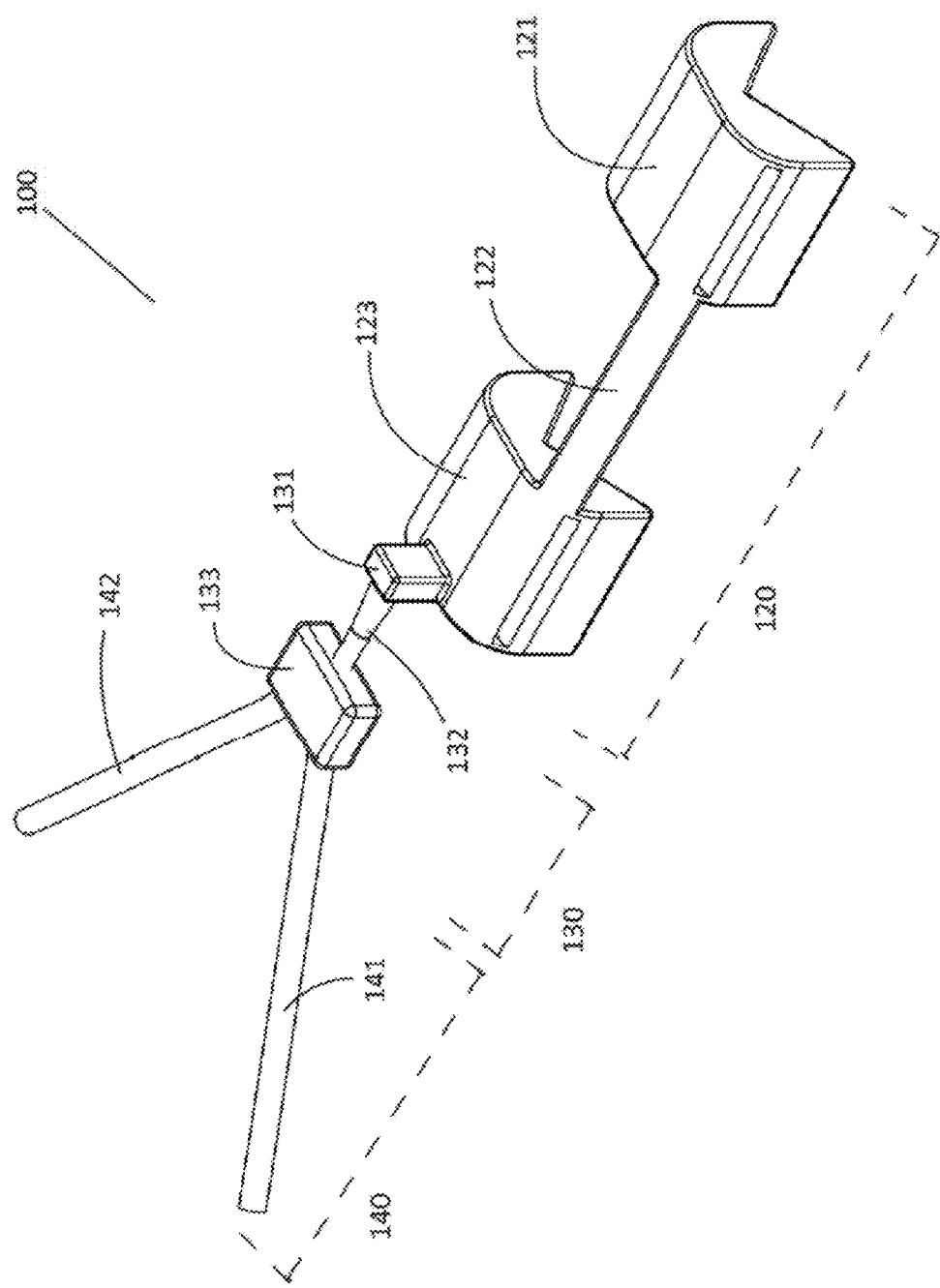
FIG. 5 is a perspective view of an imaging proxy in accordance with one embodiment.
Figure 6:
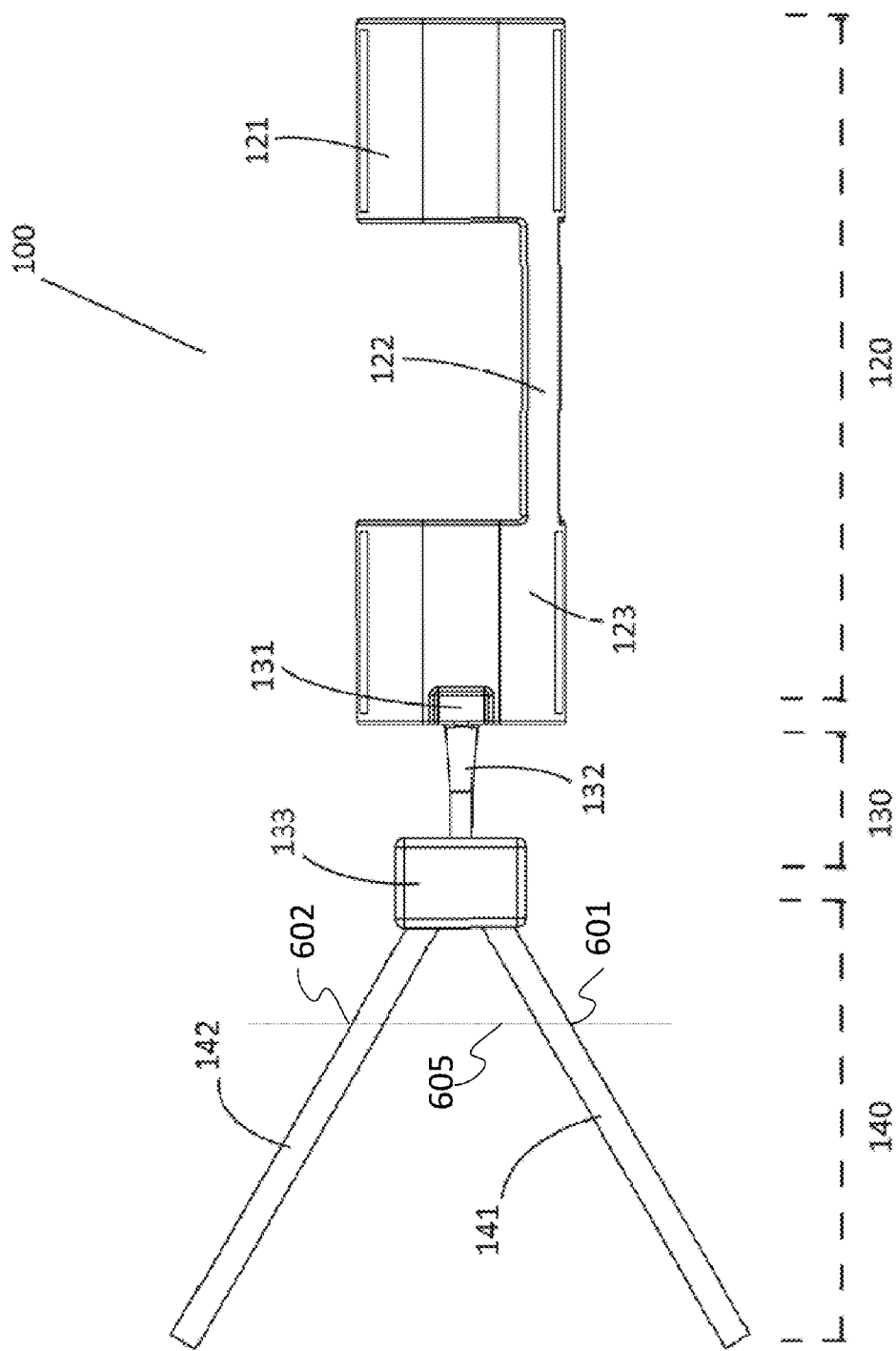
FIG. 6 is a plan view of the imaging proxy of FIG. 5.
Figure 7:
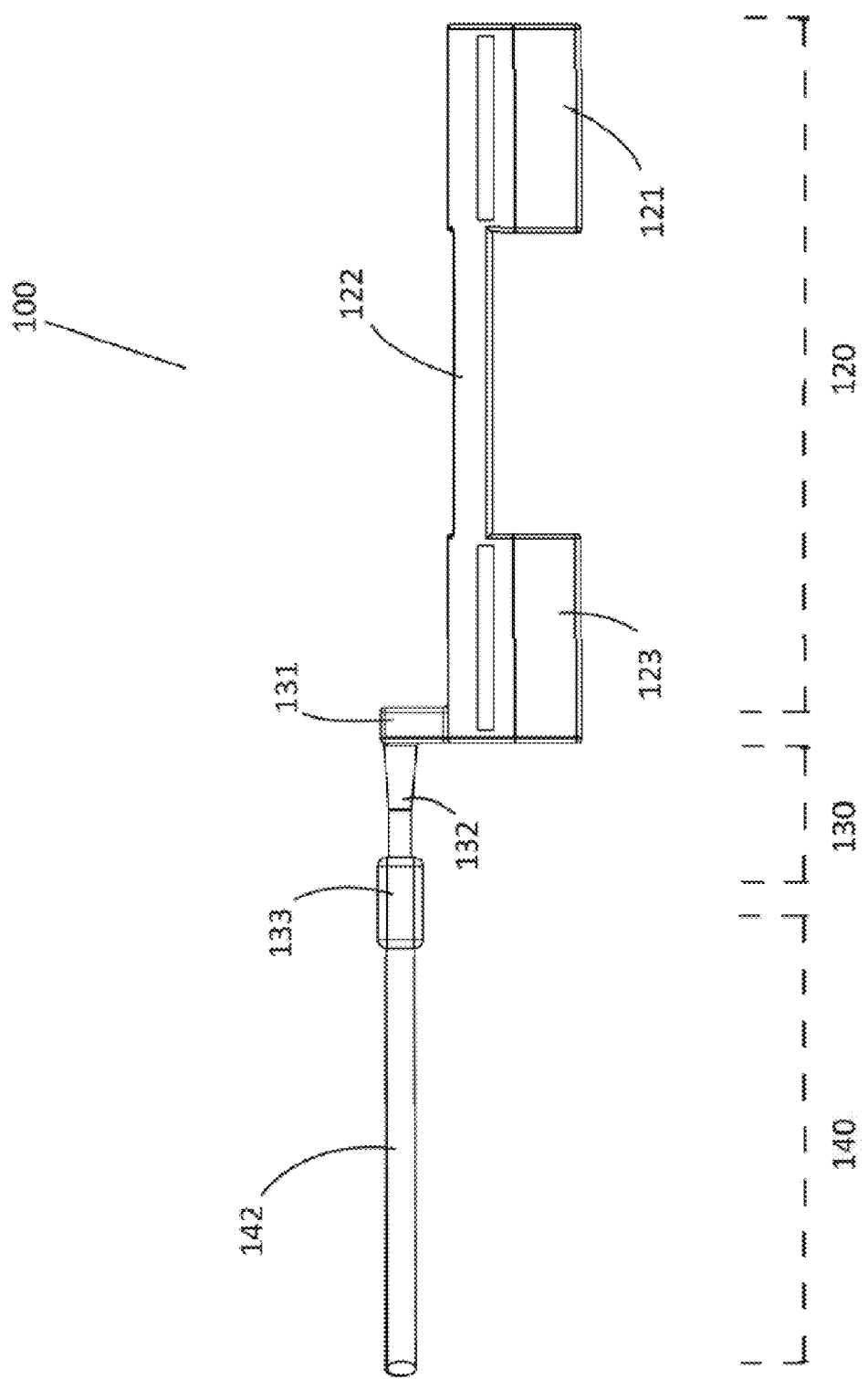
FIG. 7 is a side, elevational view of the imaging proxy of FIG. 5.

FIGS. 5-7 depict another exemplary embodiment of an imaging proxy 100. The imaging proxy 100 of FIGS. 5-7 may be one example of the imaging proxy schematically shown in FIGS. 3 and/or 4. In this example, the imaging proxy 100 includes an attachment section 120, or coupler, a connecting section 130, and a detectable section or object 140. FIG. 5 is a perspective view of the imaging proxy 100 showing the attachment section 120, the connecting section 130, and the detectable section 140. FIG. 6 is a plan view of the imaging proxy 100 showing the attachment section 120, the connecting section 130, and the detectable section 140. FIG. 7 is a side, elevational view of the imaging proxy 100 showing the attachment section 120, the connecting section 130, and the detectable section 140.

The attachment section 120, or coupler, is configured to connect (or couple) the imaging proxy 100 to a body 300 (FIGS. 2A and 2B), which may be the lower leg 500 (FIGS. 3 and 4). The connecting section 130 includes or provides a junction for the attachment section 120 and the detectable section 140. The connecting section 130 may be adjustable or otherwise configurable to allow the imaging proxy 100 to fit or accommodate a variety of joints or body parts and/or subject sizes. For example, the connecting section 130 may include one or more telescoping or other adjustable components to re-size the imaging proxy 100 to different lengths and/or heights. The detectable section 140 is the portion of the imaging proxy 100 disposed within the imaging FOV 200 to represent the body 300 (FIGS. 2A and 2B) outside of the field of view 200 (FIGS. 2A and 2B).

As shown in FIGS. 5-7, the attachment section 120 of the imaging proxy 100 includes the distal attachment 121 and the proximal attachment 123, which are connected by the frame component 122. The distal attachment 121 and the proximal attachment 123 may have a surface configured so as to securely mate with a body in a fixable position. In an embodiment, the distal attachment 121 and the proximal attachment 123 comprise a v-shaped body mounting surface. For example the V-shape mounting surface fits over the tibia to prevent rotation of the proxy member relative to the tibia. The distal attachment 121 and the proximal attachment 123 further involve slots through which belts and or straps may be passed to secure the attachment section 120 to the body. The frame component 122 may be a beam or rigid strip. In this example, the frame component 122 is offset from center. The components of the attachment section 120 may be shaped to fit around the lower leg 500. In an embodiment, the frame component 122 is offset to a side of the attachment section 120 so as to imply an L-shaped design. This configuration may allow for a better fit between the attachment section 120 and the tibia. For example, the L-shaped design may provide space between the lower leg 500 and the frame member 122. The attachment section 120 may include padding and/or other spacers between the frame and attachment components and the lower leg 500.

The distal strap 124 and proximal strap 125 may pass through slots in the distal attachment 121 and proximal attachment 123.

In an embodiment, the attachments 121, 123 and the frame component 122 may be constructed of various rigid materials, and the straps may be made of fabric. The use of plastic and fabric may avoid interfering with the data capture. For example, the materials may be selected to avoid interfering with a computed tomography ("CT") scan in the manner that, for instance, metallic materials lead to noise-related scattering.

In the example of FIGS. 5-7, the connecting section 130 includes an offset protrusion 131. The offset protrusion 131 may be configured as an offset block or riser 131. The position of the riser 131 may be adjusted to select a vertical offset between the detectable section 140 and the attachment section 120. The riser 131 may thus allow the detectable section 140 to be raised above the level of the attachment section 120 to clear another body in the imaging FOV, such as the knee and/or upper leg. In some cases, the riser 131 may be slidably engaged with the proximal connector 123. The riser 131 may be locked into position via one or more detent mechanisms, interference fits, or other structures. For example, sides of the riser 131 may be pinched by an operator to clear the detents and/or otherwise select a vertical position.

The connecting section 130 may also include a connector 132 and a mounting block 133. The extension rod 132 is disposed between the mounting block 133 and the offset block 131. In this example, the connector 132 is configured as an extension rod 132 or other axial extender. The extension rod 132 may telescopically adjust the axial position of the detectable section 140. The extension rod 132 may be axially adjustable in other ways. Other types of connectors or extenders may be used.

The components of the connecting section 130 may also be made from a plastic material or other non-interfering (e.g., non-scattering) material, such as wood. Also, metal or other materials may be used depending on the imaging and/or scanning modality employed.

The detectable section 140 includes one or more objects detectable by the imaging system. The detectable object(s) may be configured as extensions. The extensions may extend from the coupler or attachment section 120. In the example of FIG. 5-7 (and best shown in FIGS. 5 and 6), the extensions are configured as detectable bars 141, 142. The bars 141, 142 may be arranged at a known angle relative to one another and/or the attachment section 120. The bars 141, 142 may thus be arranged at a known angle relative to the body, such as the lower leg, to which the attachment section 120 is secured. The angled nature of the bars 141, 142 may define or establish a three-dimensional local coordinate system in which the location of the body outside of the FOV may be determined. For example, the location of the body may be determined through detection of the bars 141, 142 and through, for instance, triangulation. The location of the body may thus be determined for each scan from the detection of the bars 141, 142 alone.

The detectable bars 141, 142 are detectable by, or otherwise visible to, an imaging system. In some cases, the detectable bars 141,142 include or are composed of non-metallic component materials. Such materials may be useful in cases in which the imaging system implements magnetic resonance imaging ("MRI") or CT scanning. In some cases, such as those involving a CT scanner, the detectable bars 141, 142 may be composed or constructed of a borosilicate glass, such PYREX® glass. Borosilicate glass is identified well using CT scanning techniques and is relatively similar to the density of bone. Borosilicate glass may be used with other imaging techniques as well. In another embodiment, the detectable bars 141,142 may be made of wood or plastic, as well as other materials, and/or combinations thereof.

The detectable bars 141, 142 may be elongate. The size and shape of the detectable bars 141, 142 may vary. The width of the detectable bars 141, 142 may be selected to ensure or provide for detection, while minimizing the extent to which the detectable bars 141, 142 obscure the visualization of the body within the FOV. In some cases, the detectable bars 141, 142 have a length of about six inches. Other lengths may be used.

As shown in FIG. 6, in operation, the FOV of the imaging system establishes or defines a plane 605 that intersects the detectable bars 141, 142 at first and second positions 601, 602, respectively. Because the orientation (e.g., angle) of each bar 141, 142 is predetermined or otherwise known, the distance or spacing between the positions 601, 602 may be indicative of the position of the coupler or attachment section 120. Determining the spacing between the positions 601, 602 may thus be used to determine the position of the body to which the attachment section 120 is secured.

Figure 8A:
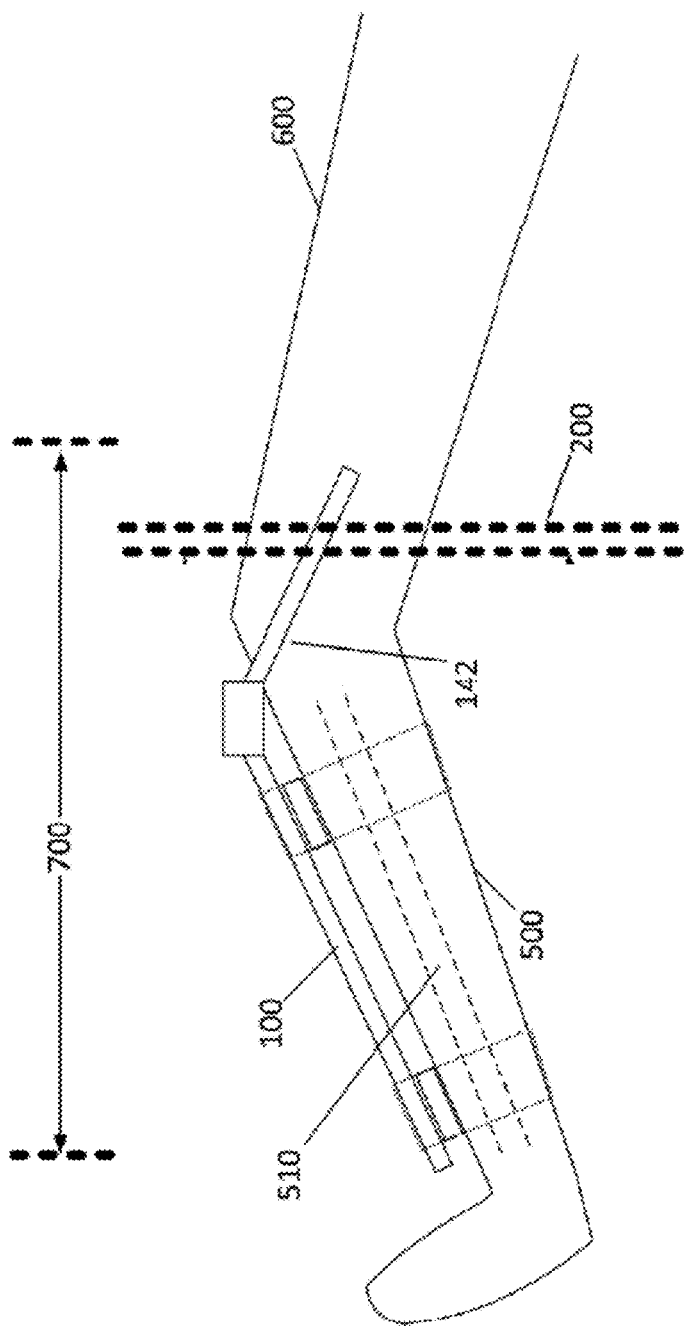
FIG. 8A is a side, schematic view of an exemplary imaging proxy disposed relative to a leg and a FOV of an imaging system in accordance with one embodiment.

FIG. 8A illustrates a lower leg 500 and an upper leg 600 with imaging proxy 100 attached along with a representation of an imaging system FOV 200. FIG. 8A also shows a representation of a long, assembled scan FOV 700. The FOV 700 may be assembled through motion of a patient table (not shown) and a construction of multiple FOV scans.

Figure 8B:
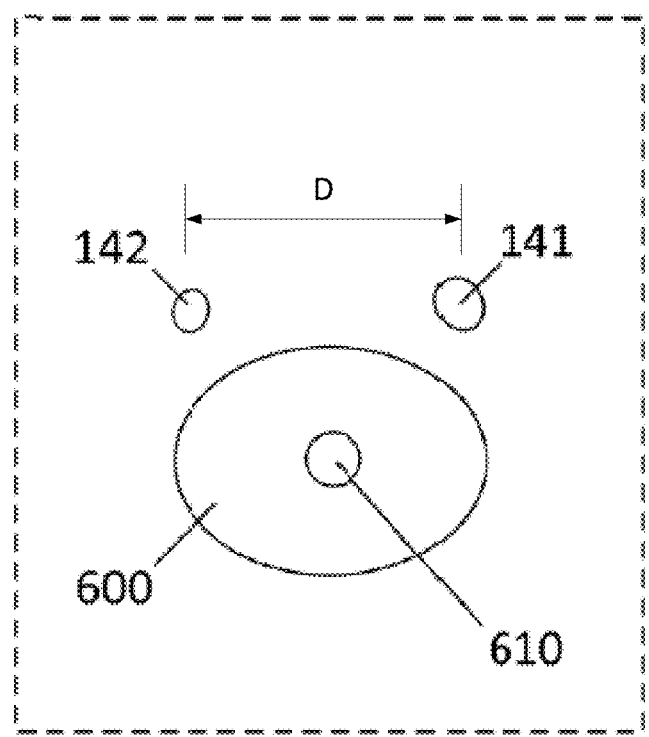
FIG. 8B is a cross-sectional view of the imaging proxy and the leg of FIG. 8A taken along the FOV.

FIG. 8B shows a transverse view of the body and an object seen in the imaging system FOV 200, which includes the upper leg 600, the femur 610, and detectable bars 141,142 of the imaging proxy 100. The distance D between the detectable bars 141, 142 may be determined. The distance D may then be used to determine the position of the lower leg 500, or tibia 510, neither of which are within the FOV. The position of the lower leg 500 may be a relative position, such as relative to the upper leg 600, or femur 610. The relative position may be measured along one or more axes, including but not limited to the lateral axes shown in FIG. 8B. Also, other geometric attributes of the detectable bars 141,142 as existent in the FOV, or combinations thereof, may be used to determine any relative linear and/or rotational position in space between the lower leg 500 and/or tibia 510, and the upper leg 600 and/or femur 610.

In operation, an imaging system, such as a CT scanner, scans the FOV and detects the two bars 141, 142 (e.g., at the positions 601, 602 shown in FIG. 6), as well as a section of the upper leg 600. As discussed further below in connection with FIG. 9, the FOV may be scanned for at least two different kinematic relationships, thus generating a kinematic or dynamic scan set. Alternatively or additionally, one or more scans may be implemented during a registration process directed to establishing the spatial relationship (e.g., distance or spacing) between the detectable bars 141, 142 and a first body, such as the lower leg. For example, a registration process may involve a long scan 700 that includes a scan of the upper leg 600, the imaging proxy 100 including at least part of the detectable bars 141, 142 and the lower leg 500. This registration process may be used to generate further scan data indicative of one or more spatial relationships between the imaging proxy 100 and the lower leg 500. The scan data and spatial relationship(s) may be used as a reference to establish positions of the lower leg 500 to the upper leg 600 in other scans of the kinematic scan set involving various lower leg 500 manipulations.

Figure 9:
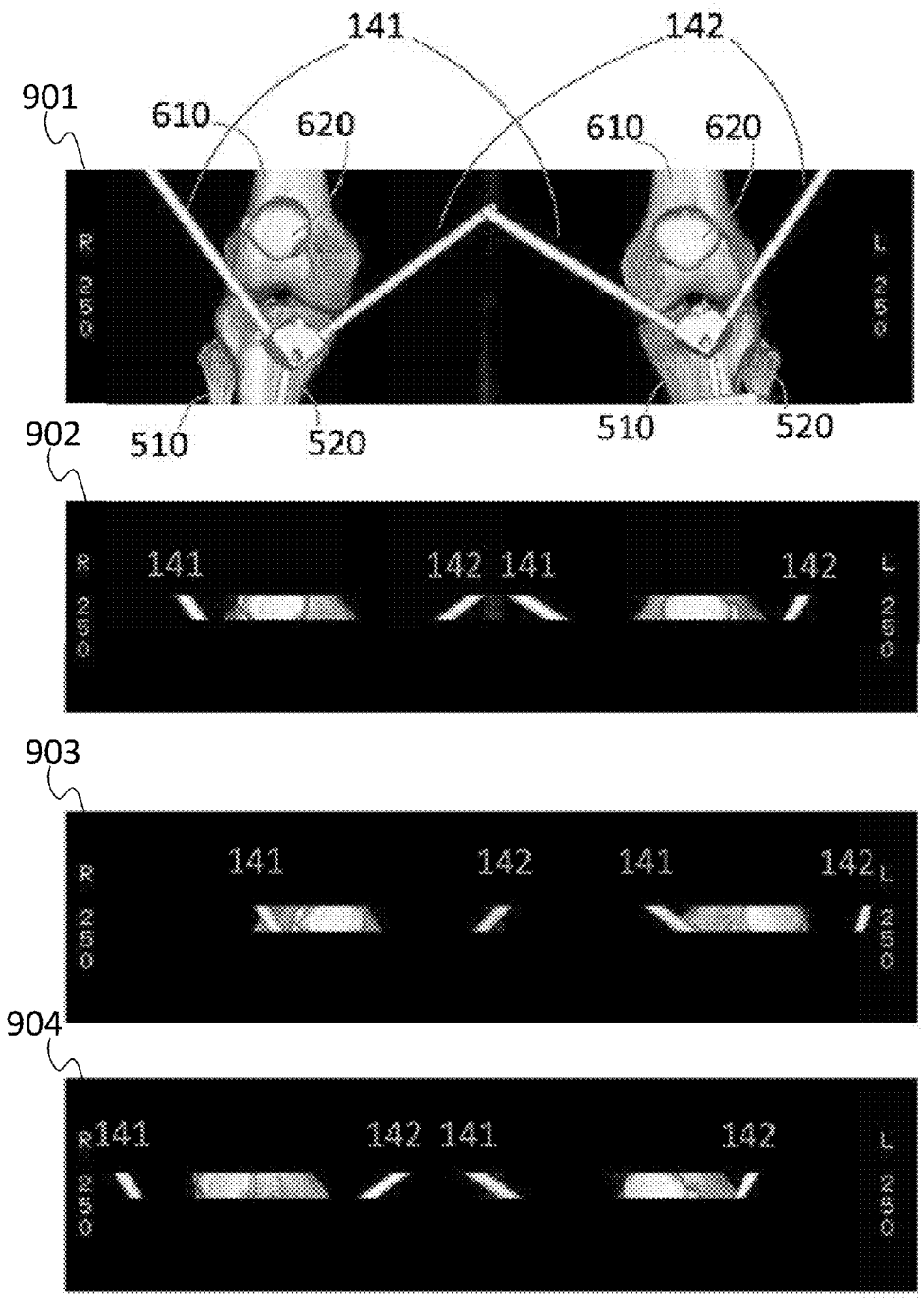
FIG. 9 shows exemplary images derived from representative scans of an imaging proxy and human body as oriented in FIG. 8A.

FIG. 9 shows an exemplary image 901 taken from the assembled long scan FOV 700 (FIG. 8A), as well as exemplary images taken from the scan area FOV 200 (FIGS. 1, 2, and 8A) of a leg in a neutral position 902, after rotation to the left 903, and after rotation to the right 904. The long FOV scan 901 may involve no limb movement. The long FOV scan 901 may be used to establish a spatial relationship between a first object, such as a lower leg or tibia 510 and the detectable bars 141, 142 of the imaging proxy. A second scan 902 may involve a short FOV that involves no limb movement (i.e., rotation). The scan 902 may also establish relative positions of a first body or tibia 520 and the detectable bars 141, 142 with the limbs in an un-manipulated or neutral position. A third scan 903 of the short FOV may involve a manipulation of one or both lower limbs. In the scan 903, the left limb is manipulated through an external rotation and the right limb is manipulated through an internal rotation. A fourth scan 904 of the short FOV may also involve a manipulation of one or both lower limbs. In the scan 904, the left limb is manipulated through an internal rotation and the right limb is manipulated through an external rotation.

Figure 10:
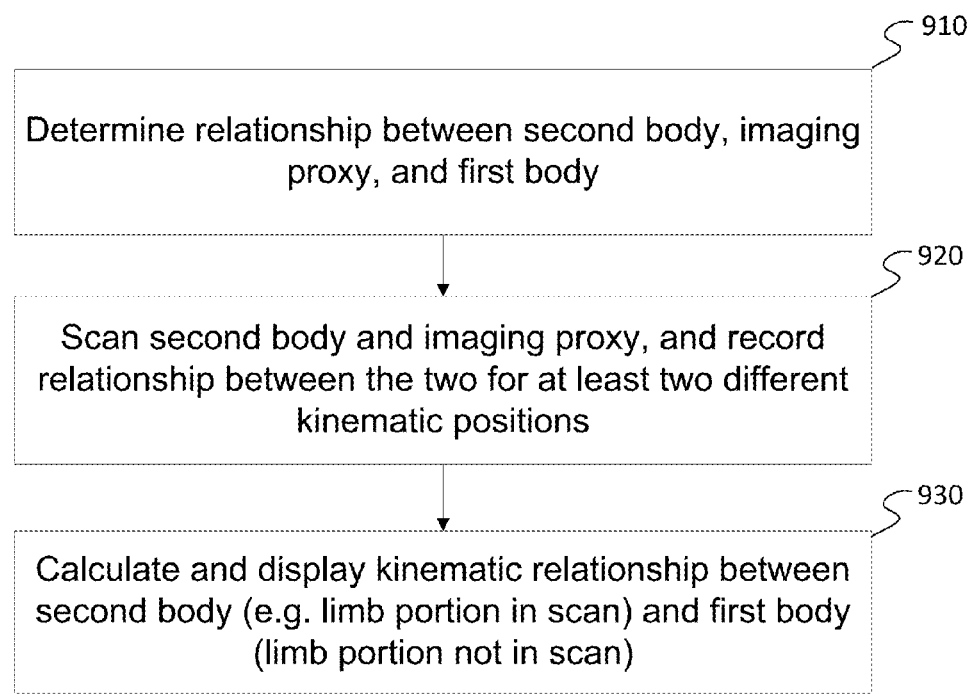
FIG. 10 is a flow chart diagram of an imaging method using an imaging proxy and including a registration process for the imaging proxy in accordance with one embodiment.

FIG. 10 is a flowchart of an embodiment in which a registration process is implemented. The registration process may be useful in connection with a kinematic scan set of images taken along a shorter scan area FOV 200 (FIGS. 1, 2, and 8A) and taken along a long scan FOV 700 (FIG. 8A). A relationship between the imaging proxy, the first body, and the second body may be established (block 910). The relationship is identified via the registration process. Registration between the structures may be achieved using any technique, such as by using the long FOV described in connection with FIGS. 8 and 9. Other techniques may also be used, for example, an attachment of the imaging proxy to a body, such as a limb, may involve a physical measurement of the positions and orientations of the imaging proxy with respect to a first body to which the imaging proxy is attached. In some cases, the position of the imaging proxy relative to the second object to be scanned may also be measured.

As described in the flowchart shown in FIG. 10, the long scan 700 may be used to establish a relationship between the limb segment (Tibia 510) that will be outside of the smaller scan area 200, the detectable bars of the imaging proxy 141,142 attached to the lower leg, and the femur 610. Kinematic scans may also be taken using the smaller scan area 200 which records data indicative of the detectable bars 141,142, the femur 610, and the patella 620. The positional relationships determined in the two scans may be used to determine, calculate, and/or display the relative positions of all of the anatomy of interest including the anatomy not present in the smaller FOV during the scanning.

One or more scans may be performed using a short FOV for an imaging system (block 920). The scans capture data indicative of the detectable object(s) of the imaging proxy and a second body, such as an upper leg. The spatial relationship between the detectable objects and the second body may be determined for at least two different kinematic positions of a first body, to which the imaging proxy is attached.

Kinematic relationships between the first body and the second body may thus be calculated and/or displayed (block 930) based on the scan data. The kinematic relationships may be calculated and displayed for each of the kinematic manipulations undertaken. Further, the kinematic relationships may be displayed proximate to, otherwise in correlation with, or part of, images rendered, displayed, or otherwise generated from the scans of the various kinematic positions.

Figure 11:
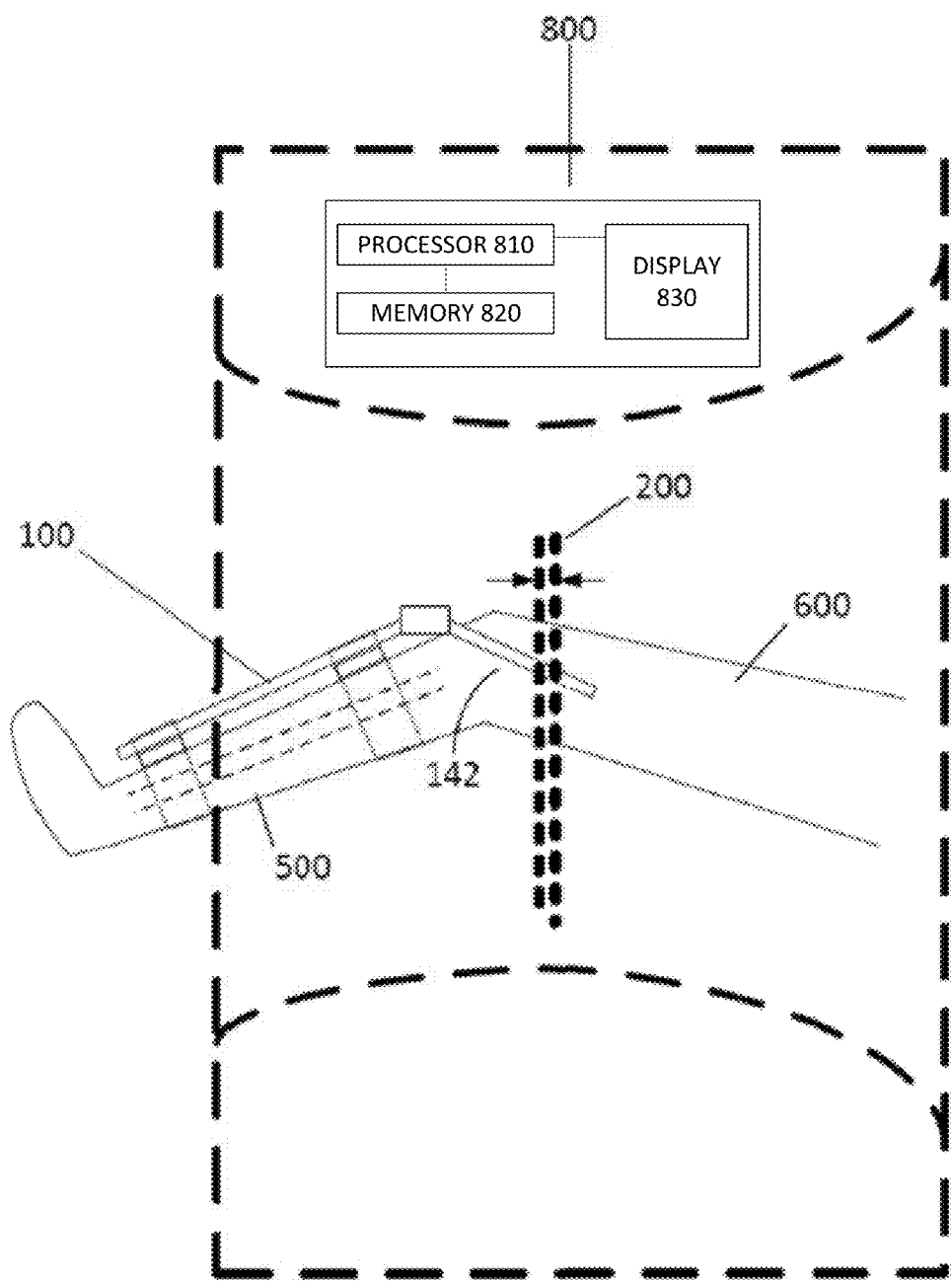
FIG. 11 is a schematic diagram of an exemplary imaging system having an imaging proxy in accordance with one embodiment.

FIG. 11 shows an exemplary embodiment of an imaging system 800 having an imaging proxy 100 attached to a lower leg 500 and extending up to an upper leg 600. The upper leg 600 is within an imaging FOV 200 of the imaging system 800, such as a CT scanner, an ultrasound system, an X-ray system, an MRI system, or any other imaging system operable to capture data representative of objects and bodies in the FOV. The imaging system 800 is configured to capture data representative of one or more objects 142 of the imaging proxy 100 and a body 600 in the FOV 200. The object 142 is positioned relative to a first body 500 outside the FOV 200.

The imaging system 800 may be used to implement multiple scans. One or more of the scans may be used for registration. For example, a long scan (as described above) may be implemented by movement of an imaging table 805. The long scan captures scan data for the whole anatomy of both the lower leg 500 and upper leg 600 to be scanned, including the tibia 510, fibula 520, patella 620, and femur 610. The second scan may be implemented without movement of the imaging table 805. The scan area of the second scan may be smaller. In this smaller scan area, the FOV is limited so that the only anatomy visible is the femur 610 and patella 620. FIG. 8B shows an example of a two-dimensional cross section image resulting from the scan of the small area FOV. An example of the process is illustrated via the images 901, 902, 903, 904 of FIG. 9. The anatomy and the detectable bars 141,142 of the imaging proxy 100 are visible in both the image derived from the extended FOV scan 901, and the images derived from the smaller field of view 902, 903, 904, in which the lower leg is manipulated into various positions.

The imaging system 800 includes a processor 810 and a memory 820. The memory 820 may include one or more instruction sets to direct the processor 810 to determine, based on the scan data, a position of the body 500 relative to the body 600. The processor 810 may be configured, via one or more of the instruction sets, to implement any calculations, computations, or other determinations described herein. The memory 820 may include any one or more non-transitory computer-readable storage memories. The processor 810 may include any one or more processors, such as a central processing unit (CPU) of a computer, a digital signal processing (DSP) unit, a graphics processing unit (GPU), or any combination thereof. The processor 810 may also be configured to render or generate an image of the scan data on a display 830 of the imaging system 800 and/or any other display device. The processor 810, memory 820, and/or display 830 may be physically integrated with other components of the imaging system, or implemented as a stand-alone computer device.

When the imaging table 805 is not moving and a scan is taken using the smaller scan area FOV, the lower leg 500 may be moved using a leg testing apparatus, other device, or a practitioner. The movement may allow for kinematic scans to be taken of the anatomy at various manipulated positions. The use of an imaging proxy during these scans allows the dynamic relationship between limb segments to be measured throughout a movement even if one limb segment is outside of the imaging FOV.

Figure 12:
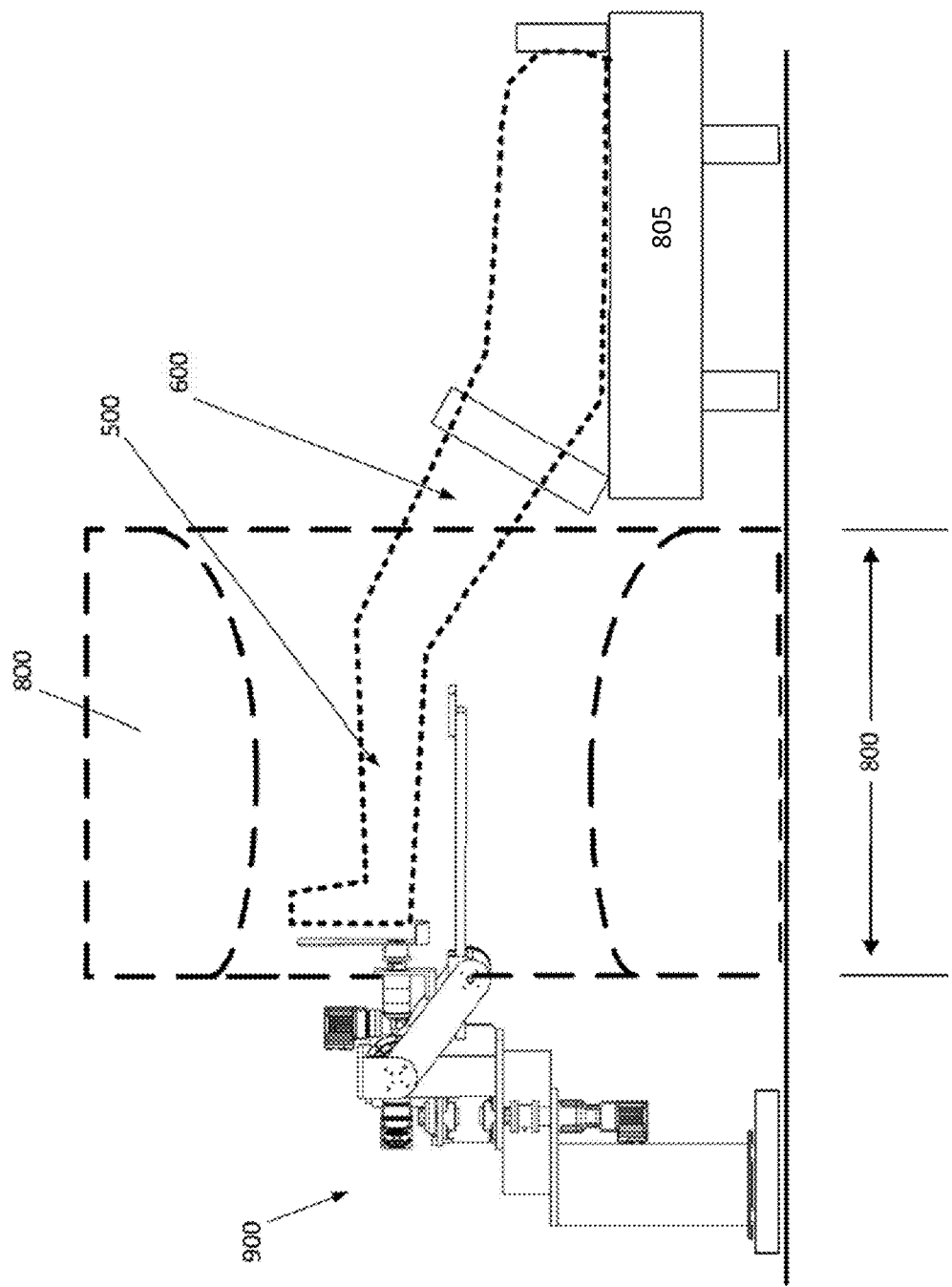
FIG. 12 is a schematic diagram of another exemplary imaging system having an imaging proxy and a knee movement test apparatus in accordance with one embodiment.

FIG. 12 depicts an exemplary embodiment of the imaging system 800, in which a body manipulation apparatus 900 is incorporated into the imaging system 800. In this example, the body manipulation apparatus 900 is configured as a leg testing apparatus 900. The leg testing apparatus 900 may include one or more processors or controllers configured to control a number of motors or other devices capable of moving the leg. The leg may be moved during imaging. In this embodiment, the leg testing apparatus 900 may be operable to manipulate the feet and lower legs 500 in order to allow for dynamic imaging of the portions of the legs (e.g., the upper legs 600) and the imaging proxy within the imaging FOV.

Further, any configuration may be used to derive spatial information of an object present outside the FOV and convey it to a region inside the FOV. In an embodiment, an apparatus may use an electromagnetic system to derive spatial information about an object outside of a FOV. In another embodiment, an apparatus may use an optical system to derive spatial information about an object outside of a FOV.

In some cases, the imaging system 800 includes an electromagnetic (EM) system (not shown) that may be used to determine the spatial relationships between the imaging proxy, the first body, and/or the second body. The EM system may include one or more transmitters (e.g., emitters) and one or more sensors (e.g., cameras or other photodetectors). The transmitters and sensors may be attached to the limb anatomy outside the FOV and/or anatomy inside the FOV. The position of the sensor(s) relative to the transmitter(s) may be tracked during the imaging to provide additional positional information for objects outside of the imaging FOV.

In some cases, the EM system may be or include an optical system. The optical system may be used to determine the spatial relationships between the imaging proxy, the first body, and/or the second body. The optical system may be implemented using either active markers that generate a light source or passive markers that are retro-reflective. These markers may be attached to the anatomy outside the FOV and/or anatomy inside the FOV. The position of the markers can be tracked to give additional positional information for objects outside of the imaging FOV.

Described above are methods, systems, and apparatus that support the measurement of two or more bodies with at least one of the bodies being outside of the FOV of the imaging system. In some cases, the bodies are in motion, and dynamic imaging of the bodies may be achieved. In some cases, the apparatus includes an attachment system, such as a coupler, rigidly attached to an object outside the FOV of an imaging system. The apparatus further includes a projected structure that extends into the FOV of an imaging system so that the position of the projected structure may be captured by the imaging system.

As described above, in some cases, a scan of a body using a smaller FOV may be registered to a scan of the same body with a larger FOV. The larger FOV scan may be taken through movement of a table on which the subject is resting, and/or movement of the imaging device itself. The smaller FOV scan may be a maximum area or volume that may be imaged without motion of the table or imaging system. To measure relative motion between two or more bodies, the table or imaging device may be stationary, thereby limiting the imaging area to the smaller FOV. Registering the body as seen in the smaller FOV to the body as seen in the long scan may provide the relationship of the body outside of the imaging area to the imaging proxy, thereby allowing for the imaging proxy to represent the body outside of the imaging FOV. The registration allows for dynamic imaging of objects both within and outside of the imaging FOV.

In accordance with some embodiments, a method for determining the relationship between a first limb portion and a second limb portion includes a determination of a relationship between the first limb portion and an imaging proxy attached to the first limb portion. The method may also include a CT or other scan of the second limb portion and the imaging proxy representing the first limb portion for at least two kinematic positions. The method may also include calculating the relationship between the first limb portion (not in the CT scan area) and the second limb portion (in the CT scan area).

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A method of imaging a subject having a first body and a second body, the method comprising:
disposing an object relative to the first body such that the object acts as an imaging proxy for the first body, the object comprising an attachment section configured to connect the object to the body, the object further comprising an extension shaped to convey orientation information;
establishing a positional relationship between the first body and the object;
after establishing the positional relationship between the first body and the object, positioning the subject in an imaging system such that the second body and the extension of the object are disposed within a field of view of the imaging system and such that the first body and the attachment section of the object are disposed outside the field of view;
after positioning the subject in the imaging system such that the first body is disposed outside the field of view, capturing, by the imaging system, a kinematic set of data indicative of the extension of the object and the second body; and
calculating a kinematic relationship of the first body relative to the second body based on the captured kinematic set of data and the positional relationship.

2. The method of claim 1, further comprising moving the first body while capturing the data.

3. The method of claim 1, wherein disposing the object comprises fixably securing the object to the first body.

4. The method of claim 1, wherein determining the location comprises determining a location of the first body relative to the second body in each of six ("6") degrees of freedom.

5. The method of claim 1, further comprising displaying an image based on the data captured by the imaging system.

6. The method of claim 1, wherein the object comprises a structure shaped such that the scan data is indicative of a rotational or linear position of the first body.

7. The method of claim 1, wherein establishing the positional relationship comprises implementing one or more registration scans of the first body and the object to generate further scan data indicative of a spatial relationship between the object and the first body.

8. The method of claim 1, wherein:
the extension is a first extension of the object;
the object comprises a second extension arranged at a predetermined angle relative to the first extension; and
positioning the subject comprises positioning the object such that the first extension and the second extension intersect the field of view at a first location and a second location, respectively.

9. The method of claim 8, wherein the first and second extensions are disposed in a V-shaped arrangement.

10. The method of claim 1, further comprising:
disposing a second object relative to a third body such that the object acts as an imaging proxy for the third body; and
positioning the third body outside the field of view and the second object within the field of view, and wherein the capturing further comprises capturing data indicative of the second object.

11. The method of claim 1, wherein establishing the positional relationship comprises implementing a registration process.

12. The method of claim 11, wherein the registration process comprises a registration scan by the imaging system.

13. The method of claim 12, wherein the field of view of the imaging system for the registration scan captures data indicative of the first body, the second body, and the object.

14. A system for imaging a subject having a first body and a second body, the system comprising:
a scanner configured to capture a kinematic set of scan data of the subject for multiple kinematic positions of the first body, the subject being positioned in the scanner such that the first body is disposed outside of a field of view of the scanner and such that the second body is disposed within the field of view;
an imaging proxy comprising a coupler configured for rigid attachment of the imaging proxy to the first body, and further comprising an extension connected to the coupler and spaced from the first body for disposition within the field of view and detection by the scanner such that the kinematic set of scan data is indicative of a position of the extension within the field of view, the extension being shaped to convey orientation information; and a processor configured to calculate, based on the kinematic set of scan data and a positional relationship between the first body and the extension, a kinematic relationship of the first body relative to the second body;

wherein the scanner is further configured to capture registration scan data indicative of the positional relationship between the first body and the extension.

15. The system of claim 14, further comprising a body manipulation apparatus configured to move the first body, the second body, or both the first body and the second body.

16. The system of claim 14, wherein the imaging proxy comprises an adjustable connector to establish a spacing between the extension and the coupler.

17. The system of claim 14, wherein the imaging proxy comprises a riser disposed between the coupler and the extension, wherein a height of the riser is adjustable to establish an offset of the coupler and the extension.

18. The system of claim 14, wherein:
the extension is a first extension of the imaging proxy;
the imaging proxy comprises a second extension; and
the first and second extensions are oriented at respective angles relative to the coupler.

19. The system of claim 18, wherein the first and second extensions are disposed in a V-shaped arrangement.

20. The system of claim 18, wherein the imaging proxy comprises a mounting block to which the first and second extensions are attached.

21. The system of claim 14, wherein the imaging proxy comprises a structure shaped such that the scan data is indicative of a rotational or linear position of the first body.

22. The system of claim 14, wherein the scanner is configured to capture data using an ultrasound technique, a computed tomography (CT) technique, a fluoroscopy technique, an X-ray technique, a magnetic resonance imaging (MRI) technique, an optical technique, an infrared technique, a magnetic tracking technique, or combinations thereof.

23. A method comprising:
disposing an object relative to a body such that the object acts as an imaging proxy for the body;
establishing a positional relationship between the body and the object;
after establishing the positional relationship between the body and the object, positioning the body and the object relative to an imaging system such that an extension of the object is disposed within a field of view of the imaging system and such that the body is disposed outside the field of view, the extension being oriented at an angle relative to the body; and
after positioning the subject in the imaging system such that the body is disposed outside the field of view, capturing, by the imaging system, a kinematic set of data indicative of the extension; and
calculating, by a processor, using the established positional relationship between the body and the object, a kinematic relationship of the body based on the captured kinematic set of data.

24. The method of claim 23, wherein:
the extension is a first extension of the object;
the object comprises a second extension; and
the first and second extensions are disposed in a V-shaped arrangement.

25. The method of claim 23, wherein establishing the positional relationship comprises implementing a registration scan by the imaging system.

* * * * *